(12) United States Patent
Cawood, Jr. et al.

(10) Patent No.: US 7,767,848 B2
(45) Date of Patent: Aug. 3, 2010

(54) METHOD OF CONTROLLING ACETIC ACID PROCESS

(75) Inventors: James M. Cawood, Jr., Houston, TX (US); Shrikant U. Kulkarni, Houston, TX (US); Lun-Kuang Liu, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 149 days.

(21) Appl. No.: 11/334,638

(22) Filed: Jan. 18, 2006

(65) Prior Publication Data

US 2006/0178528 A1 Aug. 10, 2006

Related U.S. Application Data

(60) Provisional application No. 60/650,997, filed on Feb. 8, 2005.

(51) Int. Cl.
G05B 13/04 (2006.01)
C07C 51/00 (2006.01)

(52) U.S. Cl. .................................................. 562/519

(58) Field of Classification Search ........................ None
See application file for complete search history.

(56) References Cited

U.S. PATENT DOCUMENTS

| | | | | |
|---|---|---|---|---|
| 3,769,329 | A * | 10/1973 | Paulik et al. ................. | 560/232 |
| 5,352,415 | A | 10/1994 | Ochiai ......................... | 422/105 |
| 5,374,774 | A | 12/1994 | Ochiai ......................... | 562/519 |
| 5,831,120 | A | 11/1998 | Watson et al. ................ | 562/519 |
| 6,103,934 | A | 8/2000 | Hallinan et al. .............. | 562/517 |
| 6,362,366 | B1 | 3/2002 | Hallinan et al. .............. | 562/517 |
| 6,642,413 | B2 * | 11/2003 | Thiebaut ...................... | 562/517 |

FOREIGN PATENT DOCUMENTS

| | | |
|---|---|---|
| EP | 1 002 785 | 5/2003 |
| EP | 0 983 752 B1 | 3/2004 |
| EP | 0 999 198 | 6/2004 |

OTHER PUBLICATIONS

"Model Based Predictive Control Comes to the Factory Floor" Control Engineering, 2001.*

* cited by examiner

*Primary Examiner*—Daniel M Sullivan
*Assistant Examiner*—Yevegeny Valenrod

(57) ABSTRACT

A method is disclosed for controlling a methanol carbonylation process for producing acetic acid. The method includes the steps of monitoring the rate of production of the acetic acid; reducing the production rate in response to a change in a process condition or a process equipment condition; after the production rate is reduced, controlling the process at the reduced production rate; and increasing the production rate after the condition change has been addressed until at least the production rate returns to a normal operating range; wherein during at least one of the steps of reducing the production rate, controlling the process at the reduced production rate, and increasing the production rate until the production rate returns to a normal operating range, the process is controlled by nonlinear multivariable control based on a model of the process.

Also disclosed is a process for producing acetic acid, in which at least a reaction section of the process is controlled using a multivariable nonlinear predictive controller based on a nonlinear model of the process. Control of the process is based on the same model during normal operations, during process-upset conditions and also during a recovery period after the upset has been addressed.

7 Claims, 3 Drawing Sheets

METHOD OF CONTROLLING ACETIC ACID PROCESS

CROSS-REFERENCE TO RELATED APPLICATIONS

This non-provisional patent application claims the benefit under 35 U.S.C. Section 119(e) of prior U.S. provisional application No. 60/650,997 filed Feb. 8, 2005.

BACKGROUND OF THE INVENTION

1. Field of the Invention

The present disclosure relates to control of processes for making acetic acid by carbonylation of methanol or carbonylatable derivative thereof, and particularly to process control during process upsets and during recovery therefrom.

2. Technical Background

Among currently employed processes for synthesizing acetic acid, one of the most useful commercially is the catalyzed carbonylation of methanol with carbon monoxide as taught in U.S. Pat. No. 3,769,329 issued to Paulik et al. on Oct. 30, 1973. The carbonylation catalyst contains rhodium, either dissolved or otherwise dispersed in a liquid reaction medium or supported on an inert solid, along with a halogen-containing catalyst promoter such as methyl iodide. The rhodium can be introduced into the reaction system in any of many forms, and the exact nature of the rhodium moiety within the active catalyst complex is uncertain. Likewise, the nature of the halide promoter is not critical. The patentees disclose a very large number of suitable promoters, most of which are organic iodides. Most typically and usefully, the reaction is conducted by continuously bubbling carbon monoxide gas through a liquid reaction medium in which the catalyst is dissolved or suspended.

An improvement in the prior art process for the carbonylation of an alcohol to produce the carboxylic acid having one carbon atom more than the alcohol in the presence of a rhodium catalyst is disclosed in commonly assigned U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; and European Patent No. EP 0 161 874 B2, published Jul. 1, 1992. As disclosed therein, acetic acid is produced from methanol, or a carbonylatable derivative thereof, in a reaction medium containing methyl acetate, methyl halide, especially methyl iodide, and rhodium present in a catalytically effective concentration. These patents disclose that catalyst stability and the productivity of the carbonylation reactor can be maintained at surprisingly high levels, even at very low water concentrations, i.e. 4 weight percent or less, in the reaction medium (despite the general industrial practice of maintaining approximately 14-15 wt % water) by maintaining in the reaction medium, along with a catalytically effective amount of rhodium and at least a finite concentration of water, a specified concentration of iodide ions over and above the iodide content which is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e. resistance to catalyst precipitation, especially during the product recovery steps of the process. In these steps, distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001,259, 5,026,908 and 5,144,068 are incorporated herein by reference.

As with any complex chemical process, the methanol carbonylation process described above requires monitoring and control of a number of process conditions such as methanol and carbon monoxide feed rates, reactor temperature and pressure, flasher temperature and pressure, distillation conditions, and the like. In particular, process conditions are carefully controlled to ensure that the acetic acid product is extremely pure, and in particular that it is substantially free of water, methanol and propionic acid. Consequently, when one or more of these process conditions changes suddenly due to an unexpected event such as a sudden decrease in carbon monoxide supply, failure of a catalyst pump, or the like, the production rate must be adjusted—usually downward—to ensure that the acetic acid product continues to meet quality specifications. It is desirable, however, to return to normal operating conditions as rapidly as possible after a process disturbance. It has been observed, however, that process controllers employing standard linear control algorithms do not provide sufficiently rapid recovery from large-magnitude process disturbances because the controllers are tuned to maintain control over the narrow range of "normal" operating conditions rather than the broad range resulting from a significant disturbance. In particular, linear controllers are limited in that the controller gain (i.e., the relationship between the magnitude of a deviation from target conditions associated with certain control variable(s), and the magnitude of the corrective control action achieved using manipulated variable(s)) is fixed rather than changeable. An example of a gain is the amount of steam flow change required to a heat exchanger to cause a one degree change in temperature of a process stream. During rate changes, such as upsets, the composition of the process stream will change resulting in a change in the amount of steam required to affect the one degree change in temperature. Because of this limitation of linear controllers, most multivariable predictive controllers are not capable of maintaining control and recovering quickly from large-magnitude process disturbances. Even where these controllers operate based on an empirical or theoretical model of the process, an underlying assumption of their control scheme is usually that the process gains (i.e., the magnitude of the process's response to a control action) are more or less linear. This assumption turns out to be somewhat unreliable for chemical processes, particularly where the deviation from the target conditions is very large or where a number of interrelated reactions are occurring simultaneously. This is exactly the situation in an acetic acid reactor, where in addition to methanol carbonylation, one methanol Is molecule can react (reversibly) with an acetic acid molecule to form methyl acetate and water; two methanol molecules can react to form dimethyl ether and water; and the methyl acetate can also react directly with carbon monoxide and water to form acetic acid. In fact, it turns out that at least some of the process gains for a methanol carbonylation reactor are not only nonlinear but actually change sign depending on the process conditions. During significant process upsets in a methanol carbonylation process, gains are particularly unlikely to be constant, making linear control less effective.

Notwithstanding the perceived deficiencies of linear model-based controllers for acetic acid reaction systems, it has generally not been considered appropriate to employ nonlinear controllers for this application. Until now, it has generally been thought that nonlinear controllers are best employed in environments where process setpoints are deliberately changed (e.g. to change a product grade) and the objective is to minimize the transition time between grades. Existing nonlinear control applications have focused on production of polymers where there are frequent changes in product grades. These applications have not focused on rate related changes. There remains a need, however, for control systems that are capable of managing nonlinear processes in response to unexpected disturbances so as to provide rapid recovery.

One such system now available commercially is a system from ASPEN Technology that employs two separate components to manage a process upset. In addition to a dynamic controller for maintaining control until a disruption has been addressed, ASPEN's solution employs a separate gain-scheduling component that is designed to manage the return to normal operating conditions. In effect, the gain scheduler treats the return from abnormal to normal conditions as a grade change and imposes upon the return a series of essentially linear transitions. Nevertheless, there remains a need for a control system that integrates these components. The present disclosure achieves this objective.

SUMMARY OF THE INVENTION

In one aspect, the present disclosure describes a method of controlling a process for producing acetic acid by carbonylation of methanol or a carbonylatable derivative thereof that comprises monitoring the rate of production of the acetic acid; reducing the production rate in response to a change in a process condition or a process equipment condition; after the production rate is reduced, controlling the process at the reduced production rate; and increasing the production rate after said condition change has been addressed until at least the production rate returns to a normal operating range; wherein during at least one of the steps of reducing the production rate, controlling the process at the reduced production rate, and increasing the production rate until the production rate returns to a normal operating range, the process is controlled by nonlinear multivariable control based on a model of the process. The disclosed method can maintain control during a variety of condition changes, including but not limited to one or more of the following: (a) substantial reductions in carbon monoxide availability; (b) failure of a catalyst or feed pump; (c) loss of heating or cooling capacity; (d) flooding of a downstream purification column; (e) significant deviations from expected compositions in one or more streams associated with a purification column (for example, insufficient water or excessive acetic acid in the overhead of the light ends column, which can result in loss of phase separation); (f) a shortage of storage capacity for acetic acid product; and similar changes. The method is also capable of maintaining control where the transition is a planned production rate or grade change.

In another aspect, the present disclosure describes a process for producing acetic acid by carbonylation of methanol, including the step of controlling at least a reaction section of the process and/or a purification section of the process using a multivariable nonlinear predictive controller based on a nonlinear model of the process. The controller employs the same process model to control the process during normal operations, during a process upset condition and also during a recovery period after the upset has been addressed.

BRIEF DESCRIPTION OF THE DRAWINGS

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents and alternatives falling within the scope of the invention as defined by the appended Claims.

DESCRIPTION OF ILLUSTRATIVE EMBODIMENTS

One or more illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
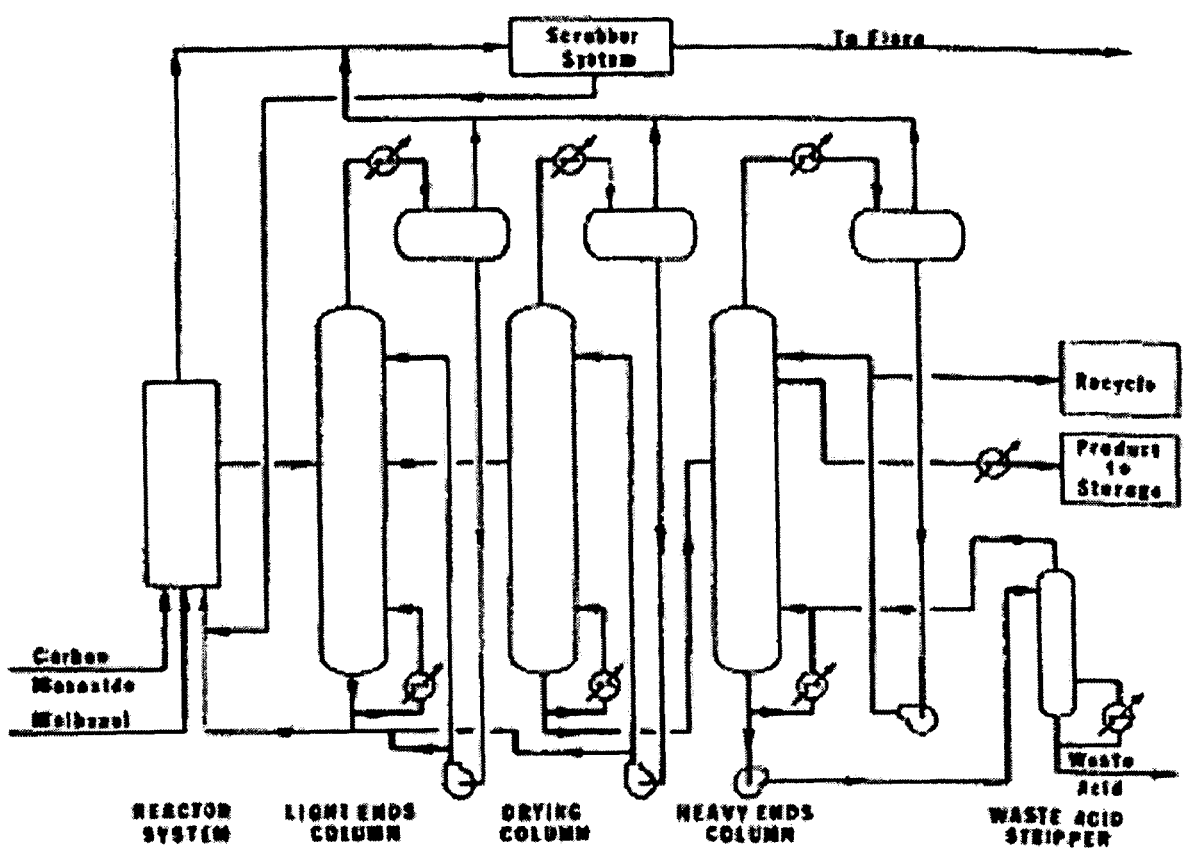
FIG. 1 is a schematic diagram of a representative methanol carbonylation process suitable for use with the present invention.

FIG. 1 depicts a commonly used methanol carbonylation process for producing acetic acid. As explained in U.S. Pat. Nos. 3,769,329 and 5,001,259, which are incorporated herein by reference, the carbonylation reaction is typically carried out by introducing carbon monoxide and a feed containing methanol, and/or a carbonylatable derivative thereof, into a stirred reactor with a catalyst, for example a rhodium or iridium catalyst, an organic iodide such as methyl iodide, and (in the case of a rhodium catalyst) an inorganic iodide such as lithium iodide as described above. The reactor effluent is flashed to recover catalyst and inorganic iodide. This is often accomplished in a separate vessel, not shown in FIG. 1, from which the residue is recycled to the reactor and the overhead product is subjected to additional purification. The product from the flash is subjected to a series of distillations to purify the acetic acid product by removing and recycling unreacted methanol, methyl acetate, and methyl iodide in a "light ends" or "splitter" column; removing water in a drying column; and (if necessary) removing propionic acid, other carbonyl-containing compounds such as crotonaldehyde, and higher alkyl iodides such as hexyl iodide in a "heavy ends" column. A number of further refinements are known; for lo example, the overhead from the light ends column typically consists of distinct heavy and light liquid phases that are separated in a "decanter" vessel and that may be separately processed (e.g. to remove alkanes or acetaldehyde) before being returned to the reactor. It is generally known that inability to maintain this liquid-liquid phase separation is indicative of certain process problems that, if uncorrected, can significantly impair the performance of the process.

It will likewise be understood that a number of other process disruptions may require a temporary reduction in the production rate of acetic acid until the problem is corrected. For example, a significant reduction in the supply of either carbon monoxide or methanol to the reactor will clearly require a reduction in the production rate. Less obviously, failure of a catalyst pump or loss of steam for heating the distillation columns may also require a temporary rate reduction. Flooding of a purification column, which indicates a composition change in the reaction system, may also require a rate reduction. As a practical matter, rate reductions may also be necessary if there is a shortage of available storage capacity for the acetic acid product.

When a process disruption requires a reduction in the acetic acid production rate, it is of course very important to minimize the duration of the rate reduction. Where a disruption is relatively minor, a typical linear multivariable predictive controller can correct it automatically; but in the case of a major disruption, the predictive model provided in the controller is typically not robust enough to correctly calculate the required corrective action. In particular, because such a controller assumes that process gains are linear, the controller output will change very slowly (and at a constant rate) to avoid overcompensation. As a result, it may take several hours, or even days, for an acetic acid process to recover from a severe process disturbance even after the disturbance itself has been addressed. When a plant is operating at or close to capacity because demand is high, extended delays in returning to full capacity may amount to millions of dollars of lost profits.

One alternative approach that has met with some success is "gain scheduling". This approach employs a limited number of distinct sets of controller tuning parameters to control discrete, well-characterized operating regions within the overall operating range of the process. In effect, this approach addresses nonlinear process gains by subdividing the process into operating regions within which the process gain is more or less linear. The two principal challenges in implementing this approach are the development of multiple, distinct sets of control parameters and accurate identification of the transition points between operating regions.

It is also extremely important to ensure that process control is maintained during a serious process disturbance. For all effective purposes, it may not be possible, or appropriate, to subdivide the recovery period into multiple linear regions. Thus, gain-scheduling systems are rendered ineffective. Gain-scheduling systems are not especially suitable for managing process disturbances because they are primarily designed to facilitate planned transitions between two operating states, not to expedite recovery from an unexpected and significant change in operating conditions. In particular, the gain-scheduling approach would effectively require a separate set of process tuning parameters for recovery from each likely disturbance. By way of contrast, a nonlinear model-based control system according to the present invention would require only a single set of control parameters because the model itself accounts for process disturbances.

As noted above, until recently the use of model-based nonlinear process control has been thought inappropriate for complex chemical processes such as methanol carbonylation because of the large number of competing reactions and the complex behavior of the process gains, as well as the high cost of developing an accurate process model suitable for implementation of nonlinear control. The Applicants have discovered, however, that nonlinear control based on an accurate process model can provide significantly faster recovery from process disturbances than a gain-scheduling or similar approach because the controller is better able to correctly predict the effect of controller output changes on the process. This faster recovery translates into increased profitability because the process returns more quickly to operation at its optimum capacity.

Figure 2:
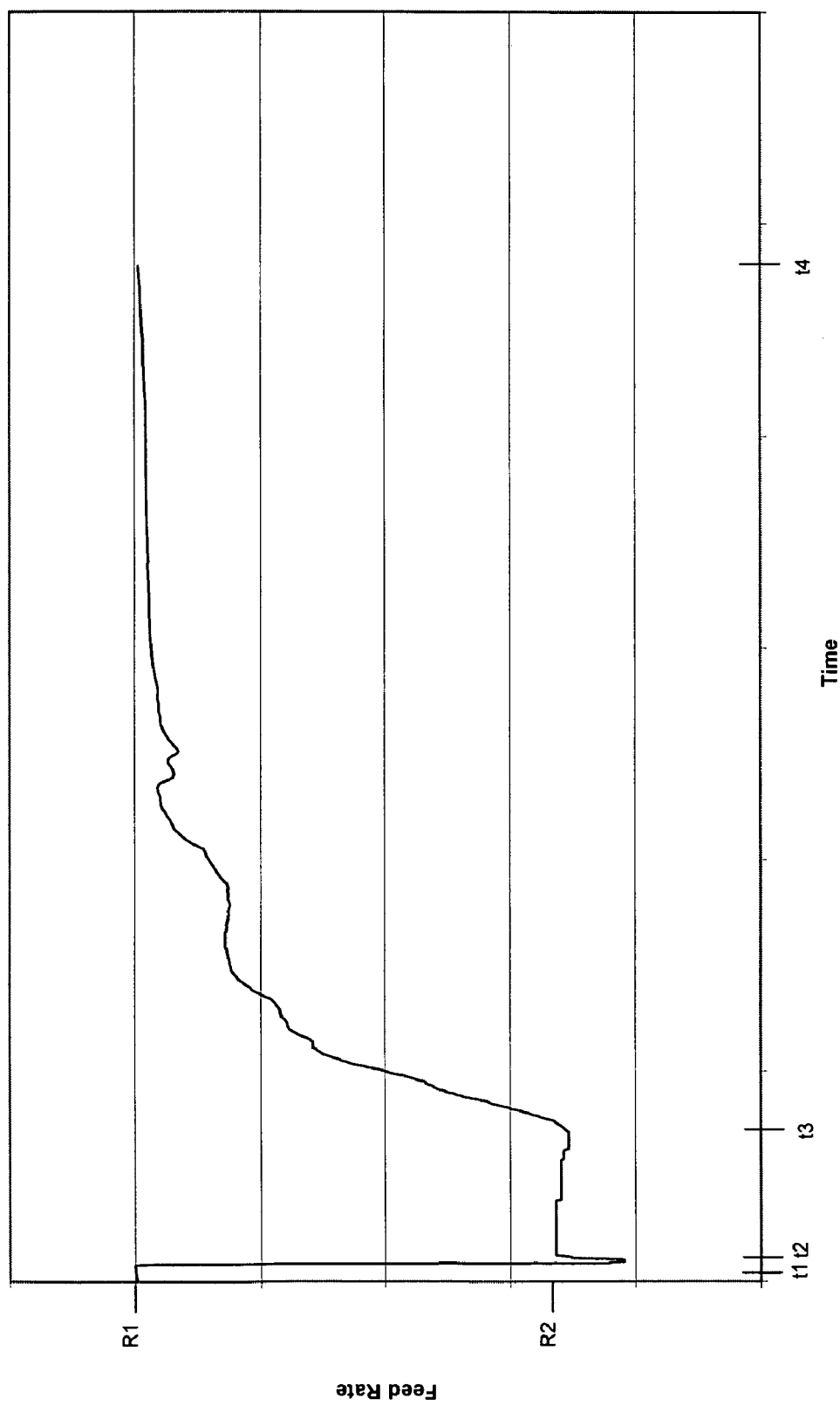
FIG. 2 is a plot of acetic acid production rate versus time for a period including a process disturbance and a recovery period thereafter expected when a nonlinear model-based controller according to one aspect of the present disclosure is used.
Figure 3:
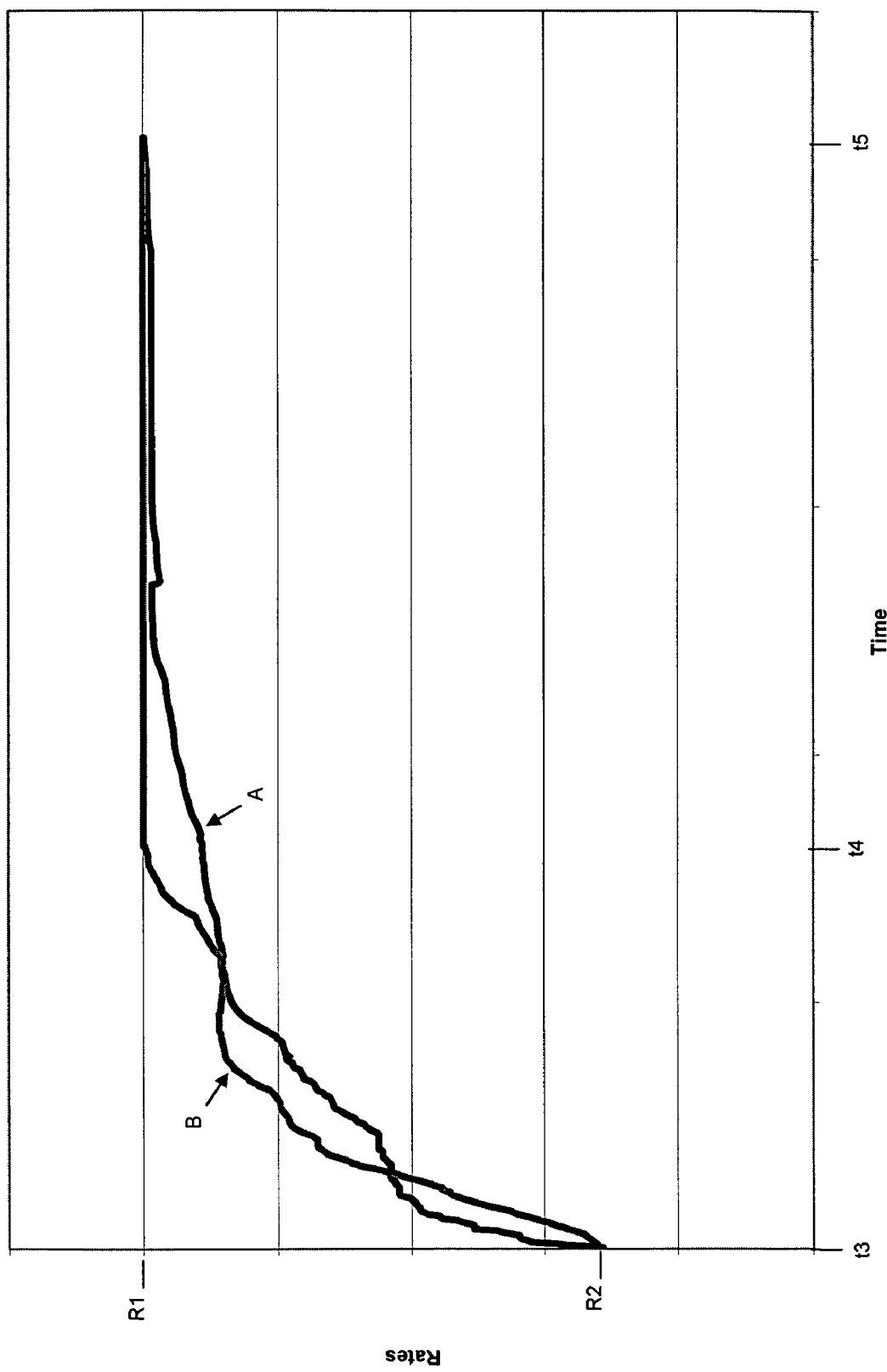
FIG. 3 is a plot of acetic acid production rate versus time for a recovery period following a process disturbance. Curve A represents the response with a combination of operator managed regulatory control followed by standard linear model-based control. Curve B represents the improved response obtained using a nonlinear model-based controller according to one aspect of the present disclosure.

This improved recovery time is depicted schematically in FIG. 2, which is a generic plot of acid production rate versus time. A target production rate RI is maintained until time t1, when a process disturbance (such as a sudden reduction in carbon monoxide supply) requires a reduction of the production rate to R2 at time t2 until t3, when the condition requiring the rate cut is corrected. Using nonlinear model-based control according to the present invention, a nonlinear multivariable controller returned the process to production rate R1 at time t4. In contrast, because a linear multivariable controller operates only over a narrow operating range, the process recovery is usually managed by a combination of linear automatic control and direct operator control. Under these conditions, the process returns more slowly to production Rate R1. Under nonlinear model-based control according to the present invention, the controller is better able to predict the effects of controller output changes, allowing a faster response. As a result, the process returns to steady state faster. This is depicted in FIG. 3, in which using linear model-based control in combination with direct operator control, the process is returned to steady state along curve A, reaching original rate R1 at a time t5. By contrast, using nonlinear model-based control in accordance with a process of the present invention, the process is returned to steady state along the steeper (i.e. faster) curve B, reaching original rate R1 at a time t4. It will be appreciated that the process recovers much faster from a process disturbance when the control system is based on an accurate nonlinear model of the process.

Nonlinear model-based control according to the present invention can, in various embodiments, also be used to control the process during the time the condition requiring the rate cut is being corrected, i.e., between time t2 and t3. Because the reduced production rate, R2, may be unique for each individual type of process upset and, indeed, for different occurrences of the same process upset, the nonlinear model-based control has benefits over a linear model-based control during this corrective period. If linear model-based control is used during this time, distinct sets of control parameters would have to be developed for each conceivable process upset. Similarly, it is contemplated that nonlinear model-based control according to the present invention can, in various embodiments, also be used to control the process during the time the production rate is being cut, i.e., between time t1 and t2.

Accordingly, the applicants have found that for the methanol carbonylation process, the perceived deficiencies of nonlinear control no longer outweigh the advantages. In particular, the high cost of developing a predictive model that fully accounts for nonlinearities in the process gains is offset by the potential cost savings resulting from the faster return to steady state that such a model allows.

Suitable control software for implementing multivariable nonlinear control includes a Galaxy Nonlinear Control system from PAS, Inc. The PAS NOVA® modeling system or a similar package may be used to develop a first-principles model of the system. This system is particularly appropriate for the acetic acid process because it is capable of modeling the complex reaction scheme in the reactor as well as the downstream separation processes. Unlike linear model predictive control systems, the Galaxy system takes account of process nonlinearities so that a single set of controller tuning parameters can be used to manage the entire process. This differs fundamentally from the "gain scheduling" approach in which separate sets of control parameters are implemented depending on the present process conditions.

It will be recognized by those of skill in the art having the benefit of this disclosure that for any specific acetic acid process the dependent variables, e.g., control variables, and independent variables, e.g., manipulated variables and external disturbances, are likely to be different. While the various process implementations are likely to have certain such dependent and independent variables in common, there are likely also to be differences among the various implementations. Similarly, the set of gains that will be of primary interest for process control will be different for each implementation of a methanol carbonylation process. While certain gains will likely be of interest to each of the process implementations, certain gains can be expected to be of importance for only certain process implementations. Likewise, the significance of any gain will for modeling purposes vary among the processes.

A typical methanol carbonylation process may have as many as 20 to 25 dependent variables associated with target conditions and as many as 15 to 20 independent variables that provide corrective control. Dependent variables that can be expected to be common to many methanol carbonylation processes include carbon monoxide supply valve output—percent open; carbon monoxide supply flow; reactor cooling valve output—percent open; reactor level; reactor to flash flow valve output—percent open; catalyst recycle flow valve output—percent open; light ends column differential pressure; light ends column overhead decanter heavy phase specific gravity; drying column differential pressures; drying column control temperature; drying column bottom section water concentration; drying column residue water concentration; drying column steam flow valve output; and drying column overhead receiver level. It will be recognized by those of ordinary skill having the benefit of this disclosure that all of these dependent variables may not be relevant to certain processes and that additional dependent variable may be relevant to certain processes.

Independent variables that can be expected to be common to many methanol carbonylation processes include methanol feed flow; reactor temperature; reactor to flasher flow; drying column control temperature; drying column overhead receiver reflux to drying column flow; drying column overhead receiver recycle to reactor flow; and drying column overhead receiver pressure. It will be recognized by those of ordinary skill having the benefit of this disclosure that all of these independent variables may not be relevant to certain processes and that additional independent variable may be relevant to certain processes.

With the number of dependent variables and independent variables that might be relevant to any particular process implementation, the number of potential gains that might be considered for nonlinear multivariable control is potentially considerable. As might be determined from modeling of the process, gains (indicated below as independent variable: dependent variable) that might be expected to be common to many methanol carbonylation process implementations include a) drying column control temperature: drying column residue water concentration; b) drying column control temperature: drying column steam flow valve output; c) drying column overhead receiver pressure: drying column differential pressures; d) drying column overhead receiver recycle to reactor flow: drying column overhead receiver level; e) drying column overhead receiver reflux to drying column flow: drying column differential pressures; f) drying column overhead receiver reflux to drying column flow: drying column control temperature; g) drying column overhead receiver reflux to drying column flow: drying column steam flow valve output; h) drying column overhead receiver reflux to drying column flow: drying column differential pressures; i) drying column pressure: drying column bottom section water concentration; j) drying column pressure: drying column control temperature; k) drying column pressure: drying column residue water concentration; l) drying column pressure: drying column steam flow valve output; m) methanol feed flow: carbon monoxide supply flow; n) methanol feed flow: carbon monoxide supply valve output—percent open; o) methanol feed flow: drying column differential pressures; p) methanol feed flow: drying column overhead receiver level; q) methanol feed flow: drying column residue water concentration; r) methanol feed flow: light ends column differential pressure; s) methanol feed flow: light ends column overhead decanter heavy phase specific gravity; t) methanol feed flow: reactor cooling valve output—percent open; u) methanol feed flow: reactor level; v) reactor temperature: light ends column overhead decanter heavy phase specific gravity; w) reactor to flasher flow: catalyst recycle flow valve output—percent open; x) reactor to flasher flow: light ends column differential pressure; y) reactor to flasher flow: reactor level; and z) reactor to flasher flow: reactor to flash flow valve output—percent open. It will be recognized by those of ordinary skill having the benefit of this disclosure that all of these gains may not be relevant to models of certain processes and that additional gains may be relevant to models of certain processes. Specific choices in gains to be included in a model will vary from process to process and will vary upon numerous factors, including, but not limited to, control objectives, control strategy, and other practical considerations, such as signal reliability. The effort to identify the gains that should be used for nonlinear multivariable control for any specific process, while possibly complex and time-consuming, would be a routine undertaking for those of ordinary skill in the art having the benefit of this disclosure.

In a particularly preferred embodiment, the model-based control system also includes real-time economic optimization capability. This feature allows the system to identify and implement control changes that optimize the production rate of acetic acid relative to the cost of feeds and utilities (e.g. steam and electricity) so that the process can operate at the most economically beneficial conditions.

To facilitate a better understanding of the present invention, the following examples of certain aspects of some embodiments are given. In no way should the following examples be read to limit, or define, the scope of the invention.

EXAMPLES

Example 1

A methanol carbonylation process, such as generally depicted in FIG. 1, was operated is in low-water mode under steady state conditions at a target production rate R1, based on methanol flow.

At time t1, the process was subjected to an upset whereby a reduction of carbon monoxide flow was experienced. At time t2, the process was being operated at a reduced production rate R2, which was 32% of the rate at R1. At that time, the process was put under multivariable nonlinear model-based control, obtained from first-principles modeling. The conditions when the process was operating at time t2, provided as either a difference from the respective conditions prior to the process upset or as a percentage of the respective condition prior to the process upset (100%), were as follows:

Temperature Difference: −12° C.
Reactor pressure: 94.6%
Carbon monoxide flow: 32%

At time t3, the carbon monoxide flow was restored. At that time, the process was being operated at a production rate that was 31% of the rate at R1. The process conditions at time t3, provided as either a difference from the respective conditions prior to the process upset or as a percentage of the respective condition prior to the process upset (100%), were as follows:

Temperature Difference: −20° C.
Reactor pressure: 100%
Carbon monoxide flow: 31%

The process was maintained under multivariable nonlinear model-based control to return the process to the previous steady state conditions associated with the target production rate R1, which was achieved at time t4. At time t4, the process conditions, provided as either a difference from the respective conditions prior to the process upset or as a percentage of the respective condition prior to the process upset (100%), were as follows:

Temperature Difference: <1° C.
Reactor pressure: 100%
Carbon monoxide flow: 100%

The recovery from the reduced production rate R2 according to this example is indicated in FIG. 2 and also by curve B in FIG. 3.

The bulk composition of the reaction medium, including, but not limited to, methyl iodide and methyl acetate levels, at times t2, t3, and t4 were essentially unchanged from those levels prior to the process upset, attesting to the ability of multivariable nonlinear model-based control to efficiently return the acetic acid process to target production rates following an upset.

Comparative Example 2

A methanol carbonylation process was operated as described in Example 1, except that at time t3, the process was put under a combination of operator managed regulatory control and multivariable linear model-based control to return the process to the previous steady state conditions associated with the target production rate R1, which was achieved at time t5. The recovery from the reduced production rate R2 according to this comparative example is indicated by curve A in FIG. 3.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. For example, the present invention is not limited to the use of processes employing rhodium as a catalyst. The present invention can be applied to systems using other catalyst systems, including processes using iridium. The depicted and described embodiments of the invention are exemplary only, and are not exhaustive of the scope of the invention. Consequently, the invention is intended to be limited only by the spirit and scope of the appended Claims, giving full cognizance to equivalents in all respects.

What is claimed is:

1. A method of controlling a process for producing acetic acid by carbonylation of methanol or a carbonylatable derivative thereof, comprising the steps of: monitoring the rate of production of the acetic acid under a set of normal operating conditions; reducing the production rate in response to an unexpected and significant change in operating conditions due to a process disturbance outside of said normal operating conditions requiring a reduction in production rate; after the production rate is reduced, controlling the process at the reduced production rate; and increasing the production rate after said condition change has been addressed until at least the production rate returns to said normal operating range; wherein during the step of increasing the production rate until the production rate returns to said normal operating range, the process is controlled by nonlinear multivariable control based on a model of the process, wherein the controlling of the process is during the severe process disturbance outside of said normal operating conditions and/or during a recovery period after the severe process disturbance outside of said normal operating conditions has been addressed, wherein the unexpected and significant change in operating conditions due to a process disturbance outside of said normal operating conditions requiring a reduction in production rate results from a condition change selected from the group consisting of:
(a) a reduction in the supply of carbon monoxide and/or methanol to the reactor in an amount sufficient to require a reduction in production rate greater than experienced during said normal operating conditions;
(b) failure of a mechanical pump;
(c) loss of heating or cooling capacity;
(d) flooding of a downstream purification column;
(e) a shortage of storage capacity for acetic acid product; and combinations thereof.

2. A method according to claim 1, wherein the process model comprises a dynamic model of at least a reaction section of the process.

3. A method according to claim 1, wherein the process model comprises a dynamic model of at least a purification section of the process.

4. A method according to claim 1, wherein the process model comprises a first-principles model of at least a reaction section of the process.

5. A method according to claim 1, wherein the process model comprises a first-principles model of at least a purification section of the process.

6. A method according to claim 1, further comprising the step of continuously optimizing process conditions based on the process model when the production rate is within a normal operating range.

7. A method according to claim 6, wherein said optimizing step balances an economic value associated with increased or decreased production rate against a changed cost of raw materials and energy associated with the increased or decreased rate.

* * * * *